(12) United States Patent
Chen et al.

(10) Patent No.: US 7,994,158 B2
(45) Date of Patent: Aug. 9, 2011

(54) **METHOD FOR INHIBITING TUMOR GROWTH WITH DEHYDROSULPHURENIC ACID EXTRACTED FROM *ANTRODIA CINNAMOMEA***

(75) Inventors: Yu-Jen Chen, Taipei (TW); Cheng-Jen Chou, Taipei (TW); Tun-Tschu Chang, Taipei (TW)

(73) Assignee: Mackay Memorial Hospital, Taipei (TW)

( * ) Notice: Subject to any disclaimer, the term of this patent is extended or adjusted under 35 U.S.C. 154(b) by 230 days.

(21) Appl. No.: 12/265,599

(22) Filed: Nov. 5, 2008

(65) Prior Publication Data

US 2009/0318400 A1  Dec. 24, 2009

(30) Foreign Application Priority Data

Jun. 18, 2008 (TW) ................................ 97122699 A

(51) Int. Cl.
*A01N 45/00* (2006.01)
*A61K 31/56* (2006.01)

(52) U.S. Cl. ........................................ 514/182; 514/169
(58) Field of Classification Search .................. 514/182, 514/169
See application file for complete search history.

(56) References Cited

OTHER PUBLICATIONS

Yang et. al. (Phytochemistry (1996) 41:1389-1392).*

* cited by examiner

*Primary Examiner* — Marcos Sznaidman
(74) *Attorney, Agent, or Firm* — WPAT, P.C.; Anthony King

(57) ABSTRACT

The present invention relates to a method for inhibiting tumor growth, in particular to the method using dehydrosulphurenic acid to inhibit the growth of leukemia cell or pancreatic cancer cell by a compound extracted and purified from *Antrodia cinnamomea*. Dehydrosulphurenic acid of the invention can be used as a pharmaceutical composition to inhibit the tumor growth of leukemia or pancreatic cancer.

4 Claims, 12 Drawing Sheets

(2 of 12 Drawing Sheet(s) Filed in Color)

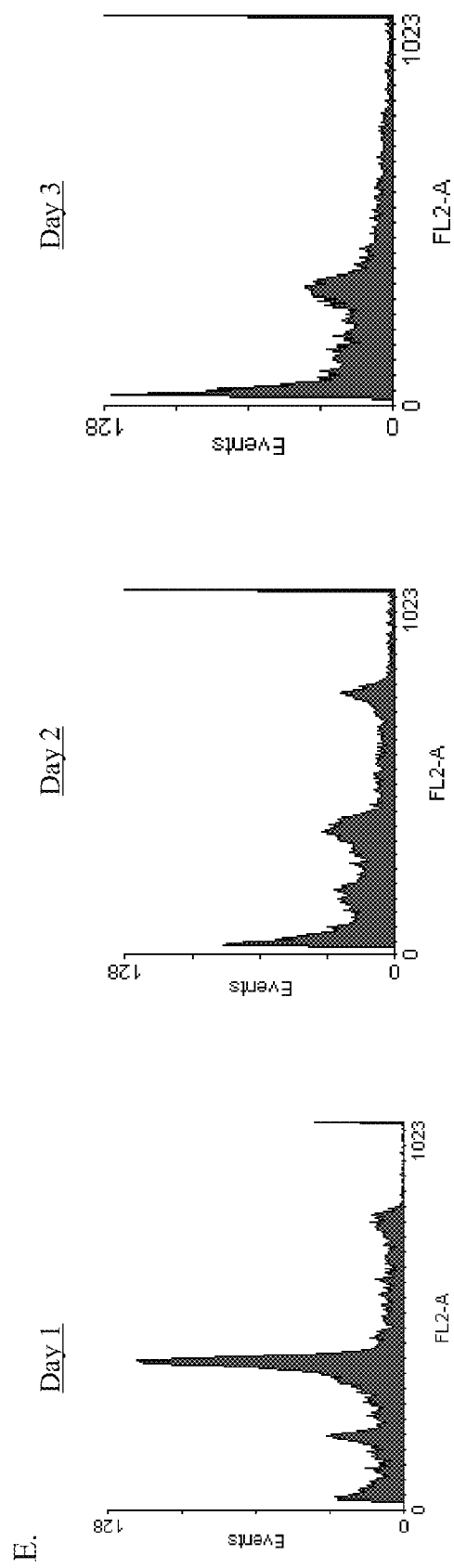

A.

B.

C.

D.

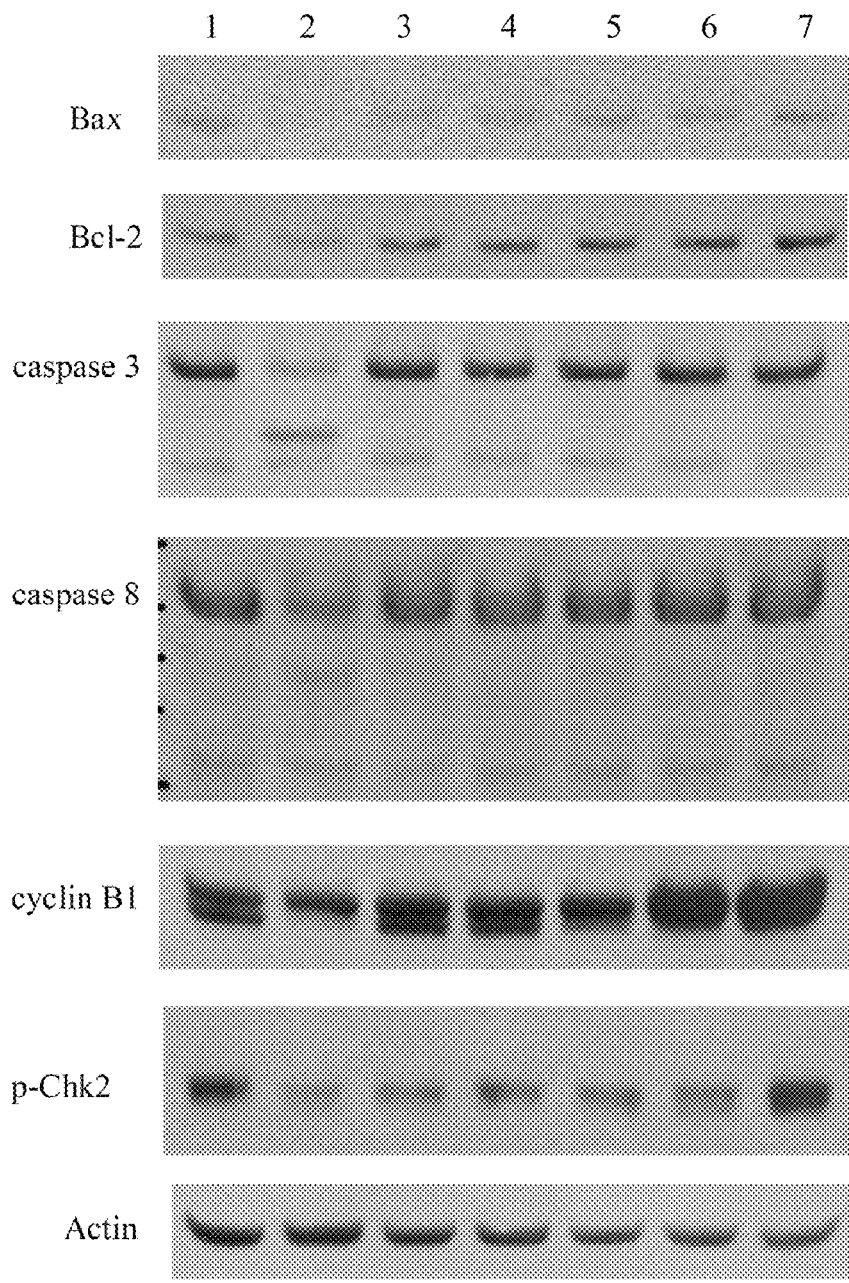

METHOD FOR INHIBITING TUMOR GROWTH WITH DEHYDROSULPHURENIC ACID EXTRACTED FROM *ANTRODIA CINNAMOMEA*

BACKGROUND OF THE INVENTION

1. Field of the Invention

The present invention relates to a method for inhibiting tumor growth, in particular to the method for inhibiting the growth of leukemia cell or pancreatic cancer cell by a compound extracted and purified from *Antrodia cinnamomea*.

2. The Prior Arts

*Antrodia cinnamomea* is a perennial mushroom belonging to the order Aphyllophorales and the family Polyporaceae, which is also known as Niu Chang-Zhi, Chang-Ku, Red-Chang, Red Chang-Zhi and the like. It is an endemic medicinal mushroom in Taiwan growing on the inner rotten heart wood wall of the only host, *Cinnamomum kanehirae*, The extremely slow growth of fruiting bodies of *Antrodia cinnamomea* and the rarely distributed natural *Cinnamomum kanehirae* make the wild *Antrodia cinnamomea* be difficult to get and expensive. In traditional Taiwanese medicine, *Antrodia cinnamomea* is commonly used in detoxification, especially effective in treatment food poisoning and drug poisoning. It has a long folk history in treating hepatic viral infection and liver diseases.

*Antrodia cinnamomea* has many complicated compounds as general edible and medicinal mushrooms, and many of them have been proved to have pharmacological and biological activities. Among them, fermented *Antrodia cinnamomea* extract and adenosine isolated from *Antrodia cinnamomea* prevented serum deprivation-induced PC12 cell apoptosis through suppression of JNK and p38 activities and activation of adenosine A receptors, respectively. (Lu, M. K., Cheng, J. J., Lai, W. L., Lin, Y. J., and Huang, N. K. 2008. Fermented *Antrodia cinnamomea* extract protects rat PC12 cells from serum deprivation-induced apoptosis: the role of the MAPK family. J. Agric. Food Chem., 56(3): 865-874; Lu, M. K., Cheng, J. J., Lai, W. L., Lin, Y. R., and Huang, N. K. 2006. Adenosine as an active component of *Antrodia cinnamomea* that prevents rat PC12 cells from serum deprivation-induced apoptosis through the activation of adenosine A(2A) receptors. Life Sci., 79(3): 252-258). Ethyl acetate extracted from fruiting bodies of *Antrodia cinnamomea* attenuated the invasion of hepatic cancer cells PLC/PRF/5PLC/PRF/5, and the mechanism is related to the inhibition of nuclear factor kappa B activity. (Hsu, Y. L., Kuo, P. L., Cho, C. Y., Ni, W. C., Tzeng, T. F., Ng, L. T., Kuo, Y. H., & Lin, C. C. 2007. *Antrodia cinnamomea* fruiting bodies extract suppresses the invasive potential of human liver cancer cell line PLC/PRF/5 through inhibition of nuclear factor kappa B pathway. Food Chem. Toxicol., 45(7): 1249-1257). Polysaccharides isolated from *Antrodia cinnamomea* inhibited cyclin D1 expression through inhibition of vascular endothelial growth factor (VEGF) receptor signal transduction and suppressed angiogenesis (Cheng, J. J., Huang, N. K., Chang, T. T., Wang, D. L., & Lu, M. K. 2005. Study for anti-angiogenic activities of polysaccharides isolated from *Antrodia cinnamomea* in endothelial cells. Life Sci., 76(26): 3029-3042).

Leukemia, one of hematological malignancies, is the most frequently occurring malignancy diagnosed in children, representing nearly 40% of cancer cases. The main reason for the high incidence is the rapid proliferation of immature blood affected by factors including gene, viral infection, drugs, and the like. The problems of serious side effects and high recurrence rate from leukemia treatment have made complete remission difficult though many progresses in clinical therapy have been made. The majority of pancreatic cancers are adenocarcinomas of the lining epithelium in the pancreatic ducts. It is seldom detected in its early stages because of its retroperitoneal position and no distinct symptoms. There is still no ideal treatment for pancreatic cancer due to the high incidence of recurrence and metastasis, as well as resistance to conventional chemotherapy and radiotherapy. The 5-year survival rate is less than 5% in the non-resectable patients, which makes pancreatic cancer a leading cause of cancer death. Both of the leukemia and pancreatic cancer have a low remission rate, therefore development of novel drugs for cancer treatment with little side effect is of urgent need at present.

Though *Antrodia cinnamomea* extracts were reported to have pharmaceutical effects from many studies, the application in growth inhibition of leukemia and pancreatic cancer cell was never reported so far. Searches for exact active ingredients in antitumor effect are still in the experimental stage, and are remained to be elucidated. Further experiments are needed to identify the effective composition for inhibition of tumor growth since the components of *Antrodia cinnamomea* were analyzed in succession. It will be of great beneficial in therapy of leukemia and pancreatic cancer if the tumor inhibiting components from *Antrodia cinnamomea* extracts are found and they can be applied in inhibition of leukemia and pancreatic cancer cell growth.

SUMMARY OF THE INVENTION

In order to identify the active ingredients for inhibiting cancer cell growth from the extracts of *Antrodia cinnamomea*, the compound of the formula (I) was isolated and purified in this invention. The chemical name of the compound is 24-methylenelanosta-7,9(11)-diene-3β,15α-diol-21-oic acid, also called as dehydrosulphurenic acid, which has a molecular formula of $C_{31}H_{48}O_4$ and a molecular weight of 484.

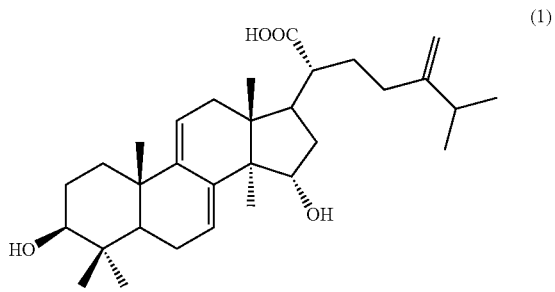

(1)

Dehydrosulphurenic acid of the invention is purified from organic solvent extracts of *Antrodia cinnamomea* fruiting bodies. The organic solvents used include, but not limited to, alcohols (such as methanol, ethanol or propanol), esters (such as ethyl acetate), alkanes (such as hexane), or halogenated alkanes (such as chloromethane or chloroethane), with ethanol being preferred.

Dehydrosulphurenic acid inhibits the growth of pancreatic cancer cell line BxPc-3 through induction of apoptosis. Dehydrosulphurenic acid also induces apoptosis and mitotic catastrophe to inhibit the growth of leukemic cell line U397.

The present invention applied the abovementioned compound to inhibit the growth of tumor cells, which was further used as a medicinal composition to treat cancer and to enhance the therapeutic effects. The compound of the invention can be applied in a range including inhibition of leukemia, pancreatic cancer cells and so on, leading to a marked slowering of the growth of cancer cells and further inhibiting proliferation of cancer cells. Finally, the compound can be applied in treatment of leukemia, pancreatic cancer and the like.

On the other hand, the Dehydrosulphurenic acid of the invention can be incorporated into medicinal compositions for treating leukemia, pancreatic cancer and the like to inhibit the tumor cell grwoth. The medicinal compositions include not only the Dehydrosulphurenic acid in effective doses, but also the pharmaceutically accepted carries. Examples of such carriers include, but are not limited to, excipients (such as water), fillers (such as sucrose or starch), binders (such as cellulose derivatives), diluents, disintegrants, absorption enhancers or sweeteners. The composition of the invention can be manufactured through mixing the Dehydrosulphurenic acid in effective doses with at least one of the carriers by means of conventional methods known in the pharmaceutically technical field, which can be formulated in the form of, but are not limited to, powder, tablets, capsules, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 Apoptosis-related protein analysis of human leukemic cells from U937 after dehydrosulphurenic acid treatment. Lane 1, untreated control cells; lane 2, cells treated with 4 μM of anti-cancer drug Camptothecin for 16 hours cells; lane 3, cells treated with 5 μg/ml of dehydrosulphurenic acid for 0.5 hour; lane 4, cells treated with 5 μg/ml of dehydrosulphurenic acid for 1 hour; lane 5, cells treated with 5 μg/ml of dehydrosulphurenic acid for 2 hours; lane 6, cells treated with 5 μg/ml of dehydrosulphurenic acid for 4 hours; lane 7, cells treated with 5 μg/ml of dehydrosulphurenic acid for 16 hours.

DETAILED DESCRIPTION OF THE PREFERRED EMBODIMENT

Figure 1:
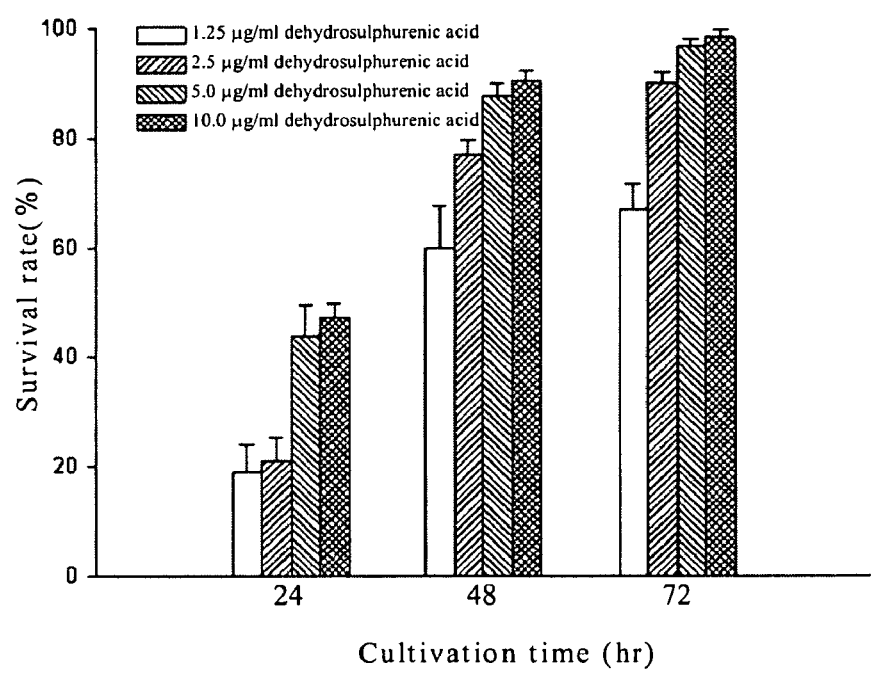
FIG. 1 Growth inhibitory rates of human leukemic cells from U937 after addition of dehydrosulphurenic acid in the concentration of 1.25, 2.5, 5, and 10 μg/ml into the culture media for 24 to 72 hours. Mean values are plotted, and vertical lines represent the S.E.M. for three independent experiments.

The fruiting bodies of *Antrodia cinnamomea* were first extracted with water or organic solvents to obtain the aqueous extract or organic solvent extract of *Antrodia cinnamomea* using the methods well known in the arts. The organic solvents used include, but are not limited to, alcohols (such as methanol, ethanol or propanol), esters (such as ethyl acetate), alkanes (such as hexane), or halogenated alkanes (such as chloromethane or chloroethane). Among them, alcohol is preferred, and ethanol is particularly preferred. The aqueous or organic solvent extracts of *Antrodia camphorate* were subjected to Diaion HP20, Silica gel, and Sephadex LH-20 column chromatography, and reverse phase RP-C18 chromatography for isolation and purification. Each fraction was recovered and applied to tumor inhibition assay. The potent fractions with tumor inhibition ability were analyzed for the structure of composition with values of NMR, MS or UV spectrum, polarimetry ratio and the like. The above approach then led to the identification of compound of formula (1) in inhibition of tumor cell growth. The compound of formula (1) is 24-methylenelanosta-7,9(11)-diene-3β,15α-diol-21-oic acid, also called as dehydrosulphurenic acid.

The anti-cancer effects of the dehydrosulphurenic acid was assessed by MTT assay according to the anti-tumor drugs screening model of National Cancer Institute (NCI) on cell survival rates using cell lines such as leukemia, pancreatic cancer and the like. The cell morphology and cell cycle were observed after the treatment of dehydrosulphurenic acid in cancer cell lines to further understand the mechanism of dehydrosulphurenic acid toward cancer cells. The above assays had proved that dehydrosulphurenic acid could decrease the growth rates of leukemic cells (including U937), pancreatic cancer cells (including BxPc-3) and the like. On the other hand, direct observation of the morphology change revealed that dehydrosulphurenic acid induced leukemia cell death in the forms of apoptosis and mitotic catastrophe. And obvious apoptosis in pancreatic cancer cells were observed after lots of round cells were shown through the treatment of dehydrosulphurenic acid. In addition, dehydrosulphurenic acid is found to result in a significant G2/M phase arrest in leukemic cells followed by an increase at S phase, while dehydrosulphurenic acid-induced cell cycle arrest of pancreatic cancer cells occurs at G0/G1 phase from the cell cycle analysis. The possible pathways of dehydrosulphurenic acid-induced inhibition of leukemia cell growth include apoptosis and mitotic catastrophe. Therefore, dehydrosulphurenic acid can be applied in growth inhibition of leukemia, pancreatic cancer cells and the like, and can further be applied in treatment of abovementioned cancers. The details of the examples are described as follows:

Example 1

Isolation of Dehydrosulphurenic Acid

Two hundred grams of fruiting bodies of *Antrodia cinnamomea* were extracted three times with distilled water at 80° C. and concentrated to get 25.4 g of a solid extract with the techniques known in the field. The residues of fruiting body were then heated and reflux for a period of 6 hours for 4 times. The extracts were filtered and the organic solvent was evaporated. The ethanol concentrate (51.8 g) was resuspended in 1.5 l of distilled water and partitioned between dichloromethane and water (volume ratio 1:1) to afford organic and aqueous fractions. The organic fraction was dissolved in methanol to get methanol dissolvable portion (38.1 g) and methanol indissolvable portion (1.21 g). The methanol dissolvable portion was subjected to Sephadex LH-20 column chromatography analysis with methanol being the mobile phase. Thin-layer chromatography (TLC) using a silica gel adsorbent on a plastic backing with a benzene/ethyl acetate/acetic acid developing solvent system was then used to isolate 5 fractions, followed by a column chromatography to yield 8 sub-fractions. The eluent solvent employed was methanol and dichloromethane in a gradient condition. The third fraction (32.1 g) was redissolved in methanol and divided into methanol dissolvable portion (30.5 g) and methanol indissolvable portion (1.1 g). The methanol dissolvable portion was subjected to High Performance Liquid chromatography (HPLC) analysis with a Cosmosil 5C18-AR-II column and a mobile phase of methanol/water/acetic acid to afford dehydrosulphurenic acid, a white powder product.

The chemical name of dehydrosulphurenic acid is 24-methylenelanosta-7,9(11)-diene-30β,15α-diol-21-oic acid, which has a molecular formula of $C_{31}H_{48}O_4$ and a molecular weight of 484. Investigation of NMR spectra showed that [α]D +60.0° (c 0.25, MeOH); $^1$H NMR (300 MHz, pyridine-d5): δ 1.90 (2H, m, H-2), 3.43 (1H, t, J=7.6 Hz, H-3), 1.32 (1H, m, H-5), 2.16 (2H, m, H-6), 6.48 (1H, br s, H-7), 5.39 (1H, d, J=6.0 Hz, H-11), 2.37 (1H, H-12β), 2.70 (1H, H-12α), 4.75 (1H, dd, J=5.9, 9.3 Hz, H-15), 1.09 (3H, s, H-18), 1.10 (3H, s, H-19), 2.23 (1H, H-25), 1.01 (3H, d, J=6.8 Hz, H-26), 0.99 (3H, d, J=6.8 Hz, H-27), 4.85 (1H, br s, H-28a), 4.88 (1H, br s, H-28b), 1.42 (3H, s, H-29), 1.17 (3H, s, H-30), 1.12 (3H, s, H-31); $^{13}$C NMR (75 MHz, pyridine-d5): δ 36.9 (t, C-1), 28.7 (t, C-2), 78.0 (d, C-3), 39.4 (s, C-4), 49.8 (d, C-5), 23.6 (t, C-6), 122.3 (d, C-7), 142.0 (s, C-8), 147.1 (s, C-9), 38.0 (s, C-10), 116.3 (d, C-11), 36.5 (t, C-12), 45.0 (s, C-13), 52.6 (s, C-14), 73.8 (d, C-15), 39.6 (t, C-16), 46.5 (d, C-17), 16.9 (q, C-18), 23.1 (q, C-19), 48.9 (d, C-20), 178.6 (s, C-21), 32.8 (t, C-22), 31.9 (t, C-23), 155.9 (s, C-24), 34.3 (d, C-25), 21.9 (q, C-26), 22.0 (q, C-27), 107.1 (t, C-28), 18.3 (q, C-29), 28.8 (q, C-30), 16.6 (q, C-31).

Example 2

In Vitro Survival Assay for Anti-Leukemia Effects

The NCI anti-cancer drug screen model was adopted to test the anti-cancer effect of dehydrosulphurenic acid. Dehydrosulphurenic acid was added into the culture media of human monoblastoid leukemic cell line U937 to test for tumor cell survival. This survival assay was carried out with the widely known MTT assay. American Type Culture Collection (ATCC) purchased U937 cell line is from lymphoma cells, which belongs to one of human leukemic cell lines and was classified into monoblasts during hematopoietic differentiation.

MTT assay is commonly used to determine cell proliferation, percent of viable cells, and cytotoxicity. MTT (3-[4,5-dimethylthiazol-2-yl]2,5-diphenyltetrazolium bromide) is a yellow dye, which can be absorbed by the living cells and be reduced to purplish blue formazan crystals by succinate tetrazolium reductase in mitochondria. Formazan formation can therefore be used to assess and determine the survival rate of cells.

The human leukemic cell line U937 was cultivated in RPMI media containing fetal calf serum for 24 hours and maintained in exponential growth condition. The proliferated cells were treated with dehydrosulphurenic acid in the concentration of 0 (the control group), 1.25, 2.5, 5, and 10 μg/ml (the experimental group), respectively. The cells were incubated at 37° C. in a 5% $CO_2$ incubator for 24-72 hours. MTT was added in a concentration of 500 μg/ml into each well in dark and incubated for 4 hours, followed by the addition of 500 μl of isopropanol to stop the reaction. The plates were read on an ELISA reader at wavelength of 570 nm to determine the survival rates. The results were reported as the average±(plus/minus) SEM (Standard Error in the Mean). For statistical analysis, the t-test were used to compare the difference between each experiment result. $P<0.05$ was considered statistically significant. Results were shown in FIG. 1.

From the result of FIG. 1, dehydrosulphurenic acid in the concentration of 1.25, 2.5, 5, and 10 μg/ml could inhibit the growth of U937 cells effectively at the first day of experiment. A positive correlation was established between the inhibition ability and the dehydrosulphurenic acid concentration. The inhibitory rates were all increased to more than 60% at the third day of experiment, with more than 95% in the concentration groups of 5 and 10 μg/ml, and up to a highest rate of 98.9%. The $IC_{50}$ value of dehydrosulphurenic acid toward U937 cells was around 2 μg/ml (data not shown). These results showed inhibitory effects of dehydrosulphurenic acid from *Antrodia cinnamomea* in leukemic cells, and the inhibitory effects were in a dose- and time-dependent manner.

Example 3

In Vitro Survival Assay for Anti-Pancreatic Cancer Effects

The NCI anti-cancer drug screen model was also adopted to test the anti-cancer effect. Dehydrosulphurenic acid was added into the culture media of human pancreatic cancer cell line BxPc-3 to test for tumor cell survival. This survival assay was carried out with the abovementioned MTT assay. American Type Culture Collection (ATCC) purchased BxPc-3 cell line is from pancreatic cancer cells, which was originated from the epithelium of human pancreatic adenocarcinomas.

The human pancreatic cancer cell line BxPc-3 was cultivated in DMEM media containing 100 IU/ml penicillin (Invitrogen, Carlsbad, Calif.), 100 IU/ml Streptomycin (Invitrogen, Carlsbad, Calif.), 2 mM glutamin (Invitrogen, Carlsbad, Calif.), 100 IU/ml penicillin (Invitrogen, Carlsbad, Calif.) and 10% fetal calf serum (Atlanta Biologicals, Norcross, Ga.). The proliferated cells were treated with dehydrosulphurenic acid in the concentration of 0 (the control group), 5 and 10 μg/ml (the experimental group), respectively. The cells were incubated at 37° C. in a 5% $CO_2$ incubator for 24-72 hours. MTT was added in a concentration of 500 μg/ml into each well in dark and incubated for 4 hours, followed by the addition of 500 μl of isopropanol to stop the reaction. The plates were read on an ELISA reader at wavelength of 570 nm to determine the survival rates. The results were reported as the average±(plus/minus) SEM (Standard Error in the Mean). For statistical analysis, the t-test were used to compare the difference between each experiment result. $P<0.05$ was considered statistically significant. Results were shown in FIG. 2.

Figure 2:
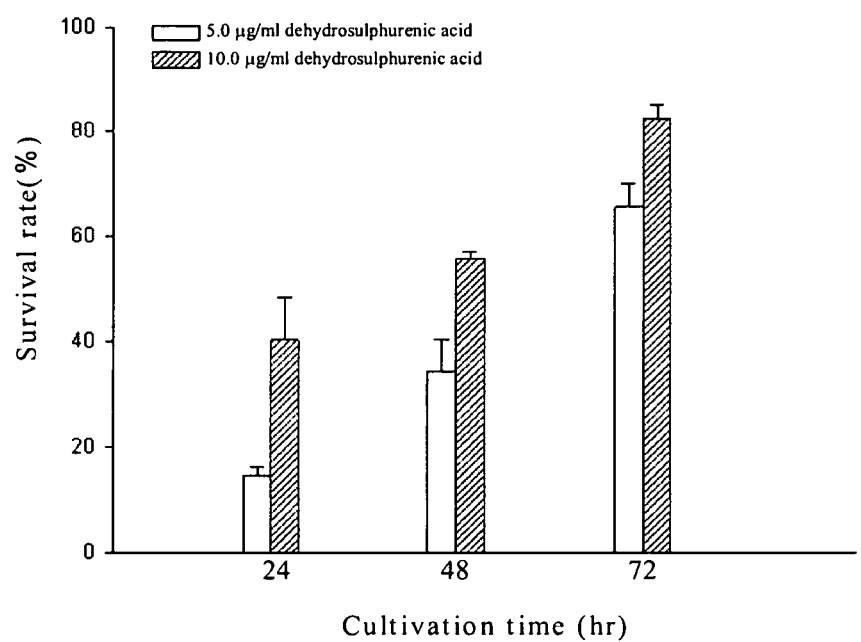
FIG. 2 Growth inhibitory rates of Human pancreatic cancer cells from BxPc-3 after addition of dehydrosulphurenic acid in the concentration of 5 and 10 μg/ml into the culture media for 24 to 72 hours. Mean values are plotted, and vertical lines represent the S.E.M. for three independent experiments.

From the result of FIG. 2, dehydrosulphurenic acid could significantly inhibit the growth of BxPc-3 cells, and positive correlations were established between the inhibition ability and the dehydrosulphurenic acid concentration or incubation time. The inhibitory rates were all increased to more than 60% at the third day of experiment in the concentration groups of 5 and 10 µg/ml, and up to a highest rate of 82.5%. The $IC_{50}$ value of dehydrosulphurenic acid toward BxPc-3 cells was around 5 µM (data not shown). These results showed inhibitory effects of dehydrosulphurenic acid from *Antrodia cinnamomea* in human pancreatic cancer cells, and the inhibitory effects were in a dose- and time-dependent manner.

Example 4

Cell Cycle Analysis on Cancer Cells after the Treatment of Dehydrosulphurenic Acid Flow cytometer was used to analyze the cell proliferation effect of dehydrosulphurenic acid toward human leukemic cell line U937 and human pancreatic cancer cell line BxPc-3.

Dehydrosulphurenic acid in the concentration of 1.25, 2.5, 5, and 10 µg/ml were used to treat human leukemic cell line U937 and the concentration of 5 and 10 µg/ml were used to treat human pancreatic cancer cell line BxPc-3; cells without addition of dehydrosulphurenic acid were served as the control group. The treated cells were fixed at 4 with 70% ethanol for 1 hour and stained for 30 min with propidium iodide solution (propidium iodide, 0.5 mg/ml; RNAse, 0.1 mg/ml) contained in a CycleTEST PLUS DNA reagent kit (Becton Dickinson, Lincoln Park, N.J.). DNA content measurement on the collected $10^4$ cells was performed on the FACS Calibur flow cytometer (Becton Dickinson, Calif., USA), and the cell cycle changes were analyzed using a ModFit software (Becton Dickinson). Results were shown in FIG. 3 and FIG. 4.

Figure 3:
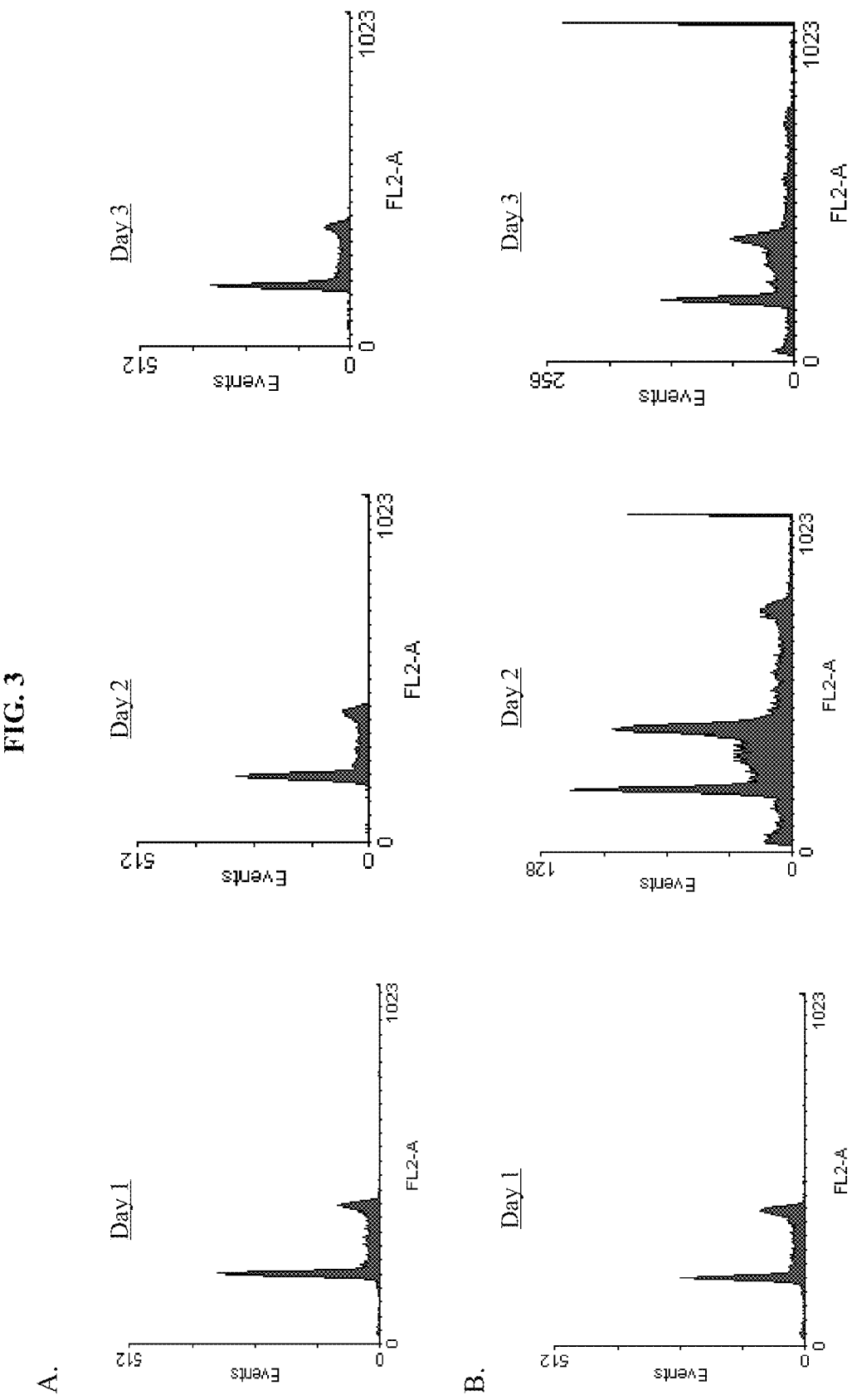
FIG. 3 Cell cycle analysis on human leukemic cells from U937 after addition of dehydrosulphurenic acid for 1 to 3 days. (A) the control group, cells without addition of dehydrosulphurenic acid for 1 to 3 days; (B) 1.25 μg/ml dehydrosulphurenic acid treatment group; (C) 2.5 μg/ml dehydrosulphurenic acid treatment group; (D) 5.0 μg/ml dehydrosulphurenic acid treatment group; (E) 10.0 μg/ml dehydrosulphurenic acid treatment group.
Figure 3:
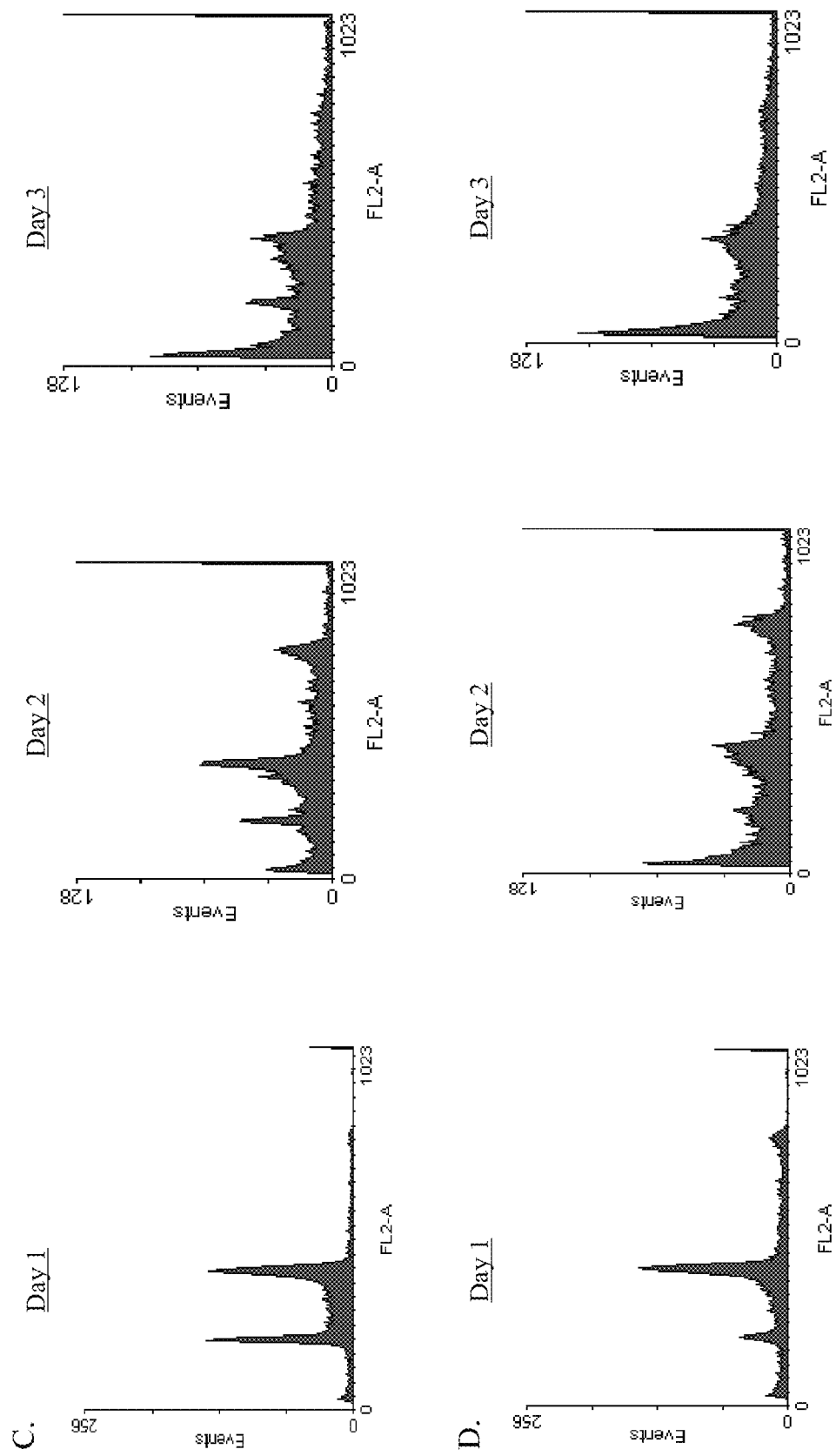

From the result of FIG. 3, remarkable G2/M phase arrest was observed in U937 cells treated with dehydrosulphurenic acid but not the untreated cells on the first day of experiment. Treatments with higher concentration of dehydrosulphurenic acid or for an extended period of time (the second day or third day of experiment) resulted in accumulating at sub-G1 population. This result showed that dehydrosulphurenic acid would induce apoptosis. Moreover, percentage of cells with polyploidy was accompanied by increasing concentration of dehydrosulphurenic acid, indicating a possible development of multinucleated cells.

Figure 4:
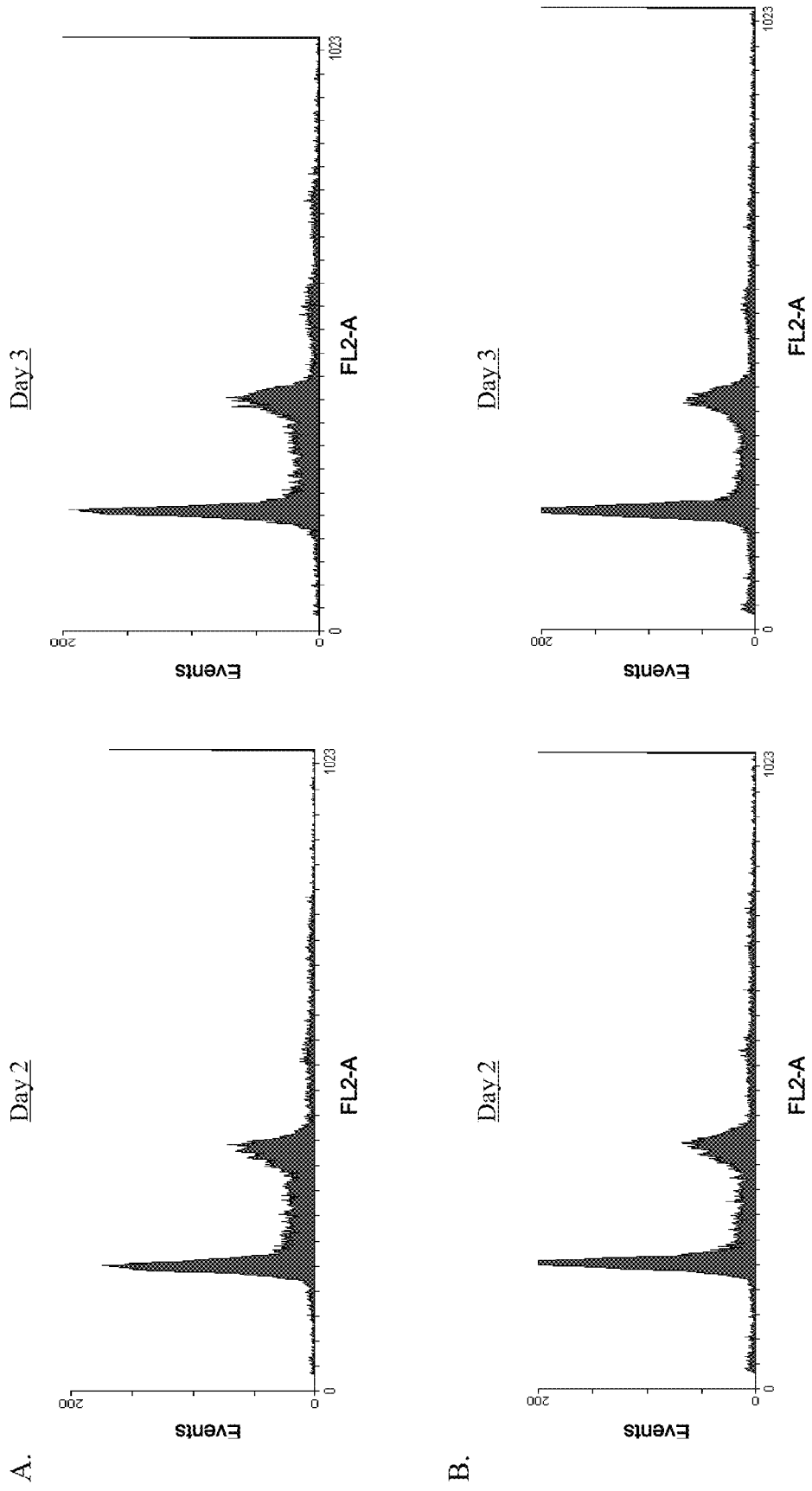
FIG. 4 Cell cycle analysis on Human pancreatic cancer cells from BxPc-3 after addition of dehydrosulphurenic acid for 2 to 3 days. (A) the control group, cells without addition of dehydrosulphurenic acid for 2 to 3 days; (B) 5.0 μg/ml dehydrosulphurenic acid treatment group for 2 to 3 days; (C) 10.0 μg/ml dehydrosulphurenic acid treatment group for 2 to 3 days.
Figure 4:
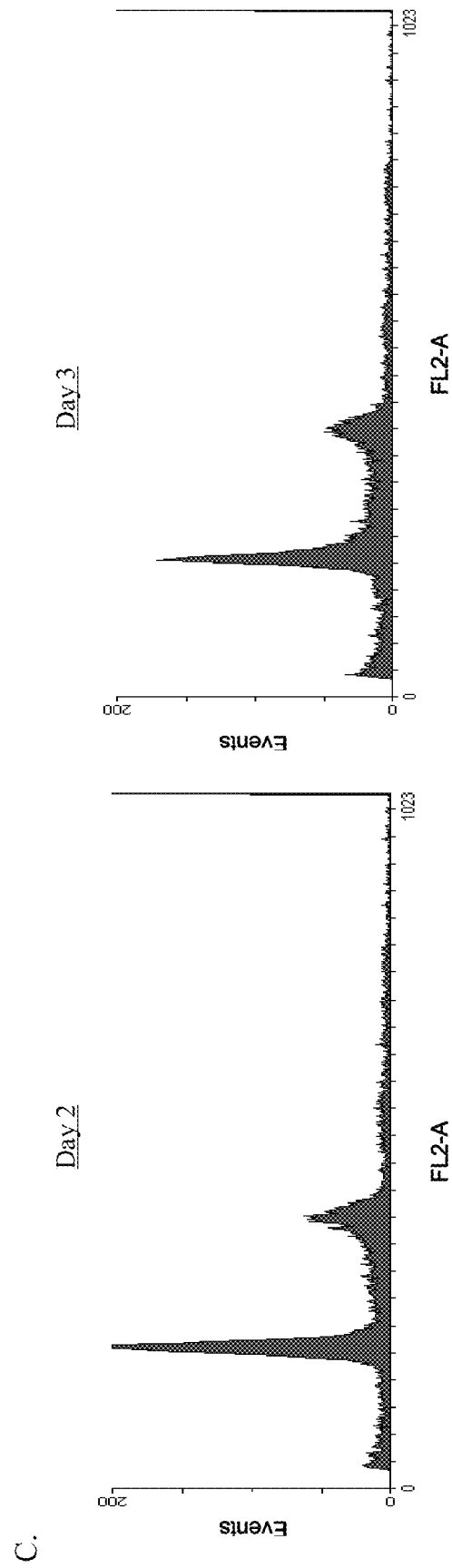

From the result of FIG. 4, remarkable G0/G1 phase arrest was observed in BxPc-3 cells treated with dehydrosulphurenic acid but not the untreated cells, and the increase of cell cycle arrest at sub-G1 population was also observed. The percentage of polyploidy cells was not changed as shown in U937. This result showed that dehydrosulphurenic acid would induce apoptosis of BxPc-3, and the cells were mainly in hypodiploid forms.

Example 5

Cell Morphology Analysis on Cancer Cells after the Treatment of Dehydrosulphurenic Acid The human leukemic cell line U937 and the human pancreatic cancer cell line BxPc-3 were treated respectively with dehydrosulphurenic acid for 24-72 h and stained with Liu's staining solution. The morphological changes of cells with (the experimental group) or without dehydrosulphurenic acid treatment (the control group) were observed under inverted phase-contrast microscope and shown in FIG. 5 and FIG. 6.

Figure 5:
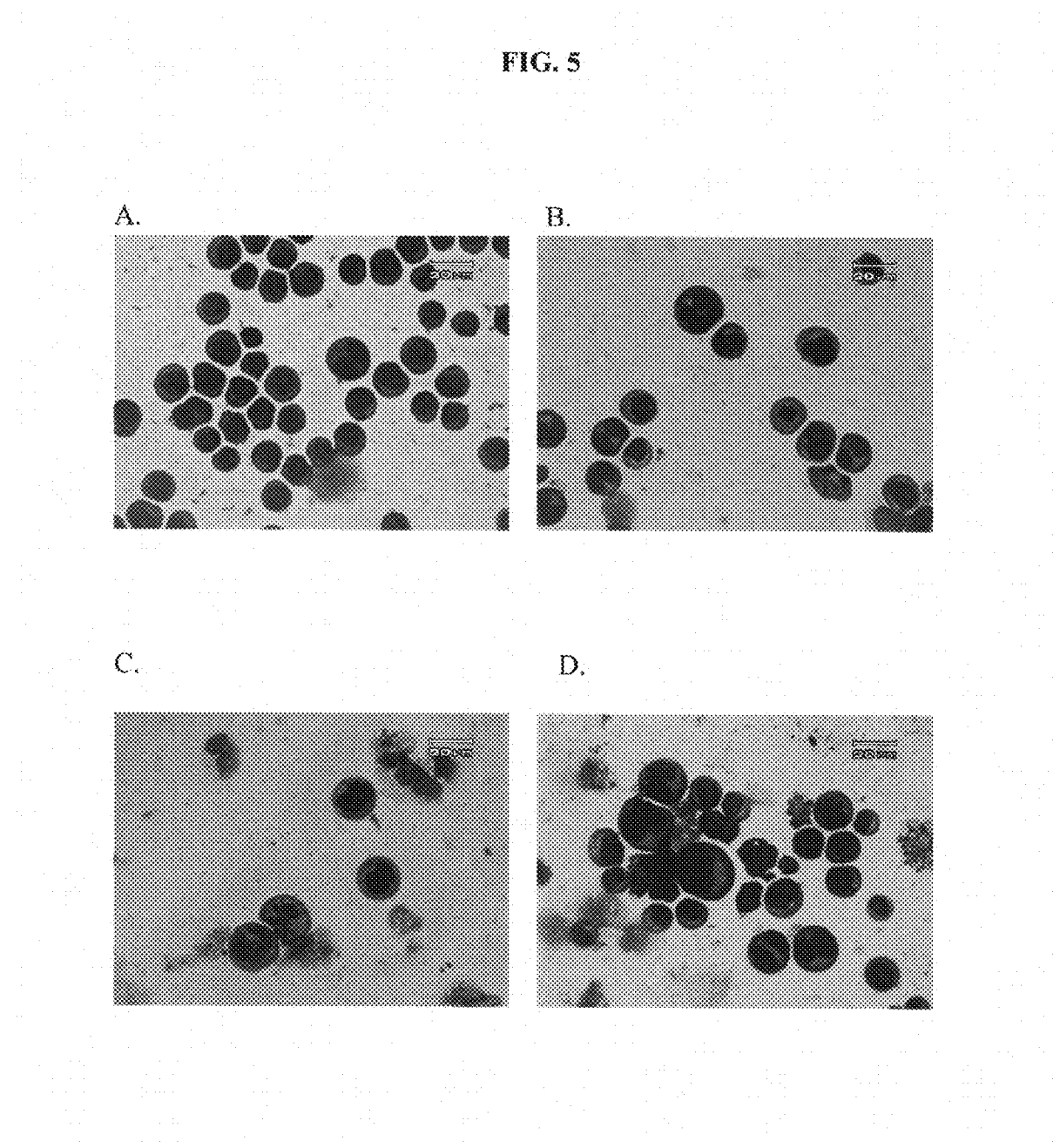
FIG. 5 Cell morphological analysis on human leukemic cells from U937 after addition of dehydrosulphurenic acid. (A) the control group; (B) 5 μg/ml dehydrosulphurenic acid treatment group for 1 day; (C) 5 μg/ml dehydrosulphurenic acid treatment group for 2 days; (D) 1.25 μg/ml dehydrosulphurenic acid treatment group for 3 days; (E) 10.0 μg/ml dehydrosulphurenic acid treatment group for 3 days. The pictures were taken with the same magnifying power. Horizontal bar: 20 μm.
Figure 6:
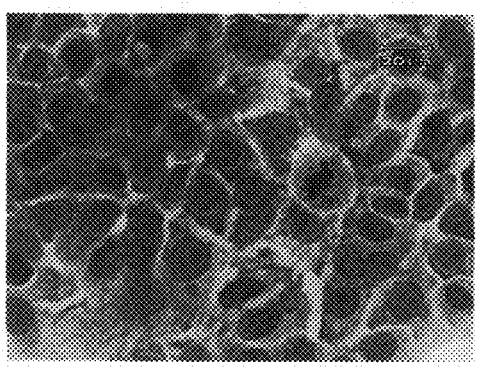
FIG. 6 Cell morphological analysis on Human pancreatic cancer cells from BxPc-3 after addition of dehydrosulphurenic acid. (A) the control group; (B) 10 μg/ml dehydrosulphurenic acid treatment group for 1 day; (C) 10 μg/ml dehydrosulphurenic acid treatment group for 2 days; (D) 10 μg/ml dehydrosulphurenic acid treatment group for 3 days. The pictures were taken with the same magnifying power. Horizontal bar: 20 μm.
Figure 6:
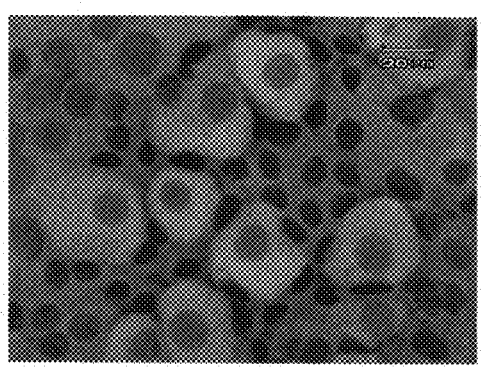
Figure 6:
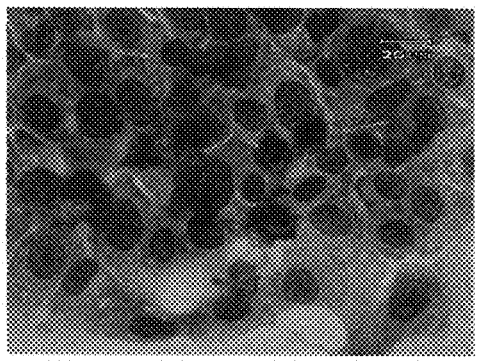
Figure 6:
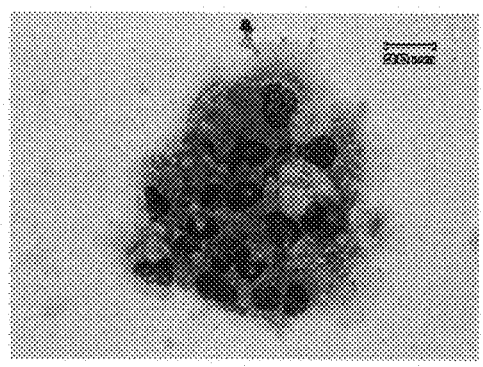

Referring to FIG. 5, U937 cells were induced to undergo apoptosis and mitotic catastrophe after the dehydrosulphurenic acid treatment. Referring to FIG. 6, the human pancreatic cancer cells from BxPc-3 had a unique morphological change: namely balloon-shaped cells were presented after the dehydrosulphurenic acid treatment for one day; and typical cell apoptosis was observed after 2 days of treatment. The ballooning of cells has been suggested as a stage of apoptosis in fibroblast-like cells treated by tumor necrosis factor-alpha (TNF-α) was reported from previous study (Okamoto, K., Mizuno, M., Nakahara, N., Natsume, A., Yoshida, J., Mori, T., Hori, S., & Kobayashi, H.2002. Process of apoptosis induced by TNF-alpha in murine fibroblast Ltk-cells: continuous observation with video enhanced contrast microscopy. *Apoptosis.*, 7(1): 77-86). Therefore, dehydrosulphurenic acid could cause the apoptosis of the human pancreatic cancer cells from BxPc-3.

Example 6

Nuclear DNA Changes in Tumor Cells after the Treatment of Dehydrosulphurenic Acid Besides the abovementioned morphological changes, biochemical changes of the dying cell during apoptosis include chromatin condensation, cell shrinkage and breaking into apoptotic bodies, internucleosomal DNA fragmentation into a multiple DNA ladder during the late stage of apoptosis (can be shown in DNA electrophoresis) and so on. To further define the effects of dehydrosulphurenic acid on U937 and BxPc-3 during apoptotic stages, DNA ladders were determined using DNA electrophoresis at the present experiment.

Dehydrosulphurenic acid in the concentration of 5 µg/ml were used to treat human leukemic cell line U937 and human pancreatic cancer cell line BxPc-3 for 24, 48, and 72 hours; while U937 cells treated with 4 µM anti-cancer drug Camptothecin for 24 hours were served as positive control. Then these cells were lyzed with 0.5 ml of lysis buffer (5 mM Tris-borate (TBE), pH8.0; 0.25 ml Nonidet P-40; 1 mM EDTA; 20 µg/ml RNase (Sigma, St. Louis, Mo.)) at 37° C. for 1 hour, followed by treating with 300 µg/ml proteinase K for 1 hour. Total DNAs were extracted and analyzed by 1.5% agarose gel electrophoresis in TBE buffer (5 mM TBE buffer containing 1 µM EDTA, pH 8.0). The gel was stained with ethidium bromide and visualized under UV and shown in FIG. 7.

Figure 7:
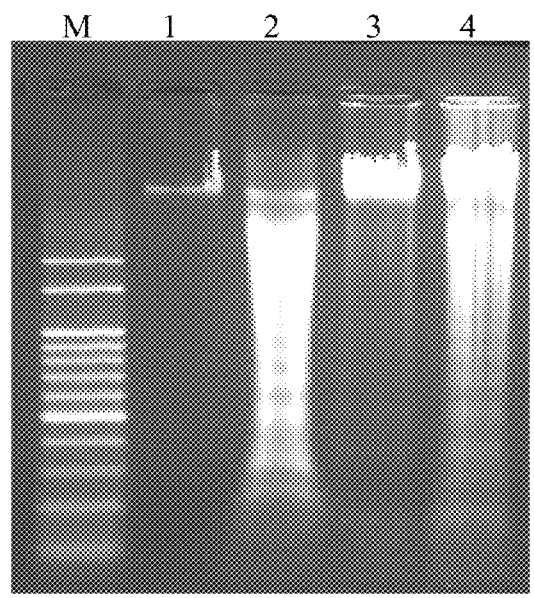
FIG. 7 DNA electrophoresis result of human leukemic cells from U937 after dehydrosulphurenic acid treatment. M, DNA marker; 1, cells treated with 4 μM of anti-cancer drug Camptothecin for 24 hours; 2, cells treated with 5 μg/ml of dehydrosulphurenic acid for 24 hours; 3, cells treated with 5 μg/ml of dehydrosulphurenic acid for 48 hours; 4, cells treated with 5 μg/ml of dehydrosulphurenic acid for 72 hours.

Referring to DNA electrophoresis result of FIG. 7, DNAs obtained from dehydrosulphurenic acid treated U937 cells showed obvious DNA ladders, as compared with the complete DNA in the postive control group. Therefore, dehydrosulphurenic acid induced apoptosis in U937 cells were related to the late apoptotic stage. On the other hand, electrophosis result of BxPc-3 cells showed no DNA ladder (data not shown).

Example 7

Mitochondrial Transmembrane Potential Changes in Tumor Cells after the Treatment Of Dehydrosulphurenic Acid Mitochondrial pathway is one of the pathways of apoptosis induction. In cells undergoing apoptosis, mitochondria were stimulated to regulate the Bcl-2 family of proteins, which made the inner and outer mitochondrial membrane unstable. Apoptigenic factors were further released to induce apoptosis. The apoptotic mechanism of dehydrosulphurenic acid in tumor cells was studied in this experiment by measuring the mitochondrial transmembrane potential.

Figure 8:
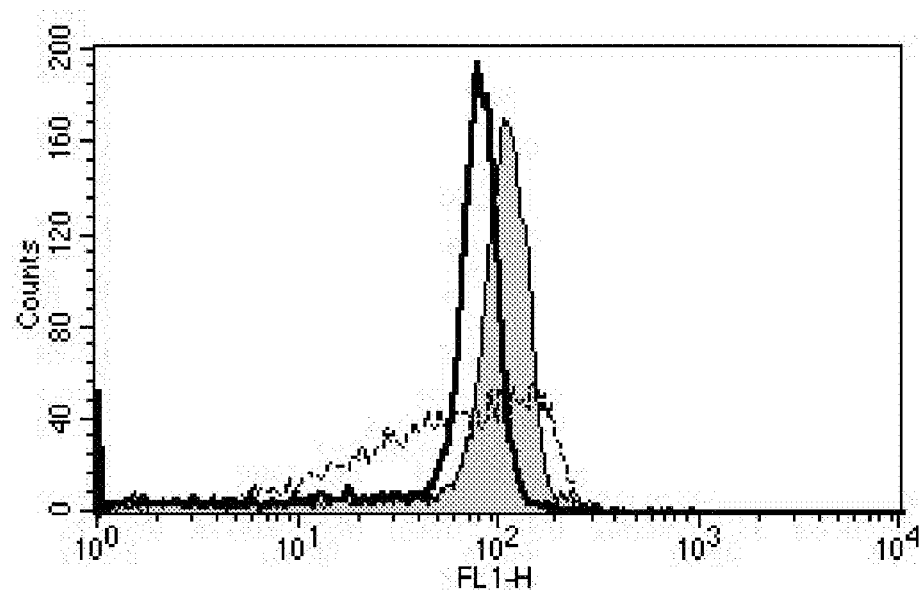
FIG. 8 Mitochondrial transmembrane potential analysis of human leukemic cells from U937 after dehydrosulphurenic acid treatment. Grey strip, the control group; solid line, cells treated with 5 μg/ml of dehydrosulphurenic acid for 16 hours; dotted line, cells treated with 4 μM of anti-cancer drug Camptothecin for 16 hours.

Dehydrosulphurenic acid in the concentration of 5 µg/ml were used to treat human leukemic cell line U937 for 16 hours; while U937 cells treated with 4 µM anti-cancer drug Camptothecin for 16 hours were served as positive control, and cells without treatment were served as negative control. These cells were washed with PBS and incubated with 40 nM 3,3'-dihexyloxacarbocyanine ($DiOC6_{(3)}$, Molecular Probes, Eugene, Oreg.) in the dark at 37° C. for 15 min, and were detected by flowcytometry. Excitation and emission wavelength settings of 488 nm and 530 nm were used to detect the density of green fluorescence to further estimate mitochondrial membrane potential. Results were shown in FIG. 8.

The mitochondrial transmembrane potential would decrease if the apoptotic process was affacted through mitochondrial pathway. The mitochondrial transmembrane potential of anti-cancer drug Camptothecin in positive control group showed a decrease of 37.1% while no significant decrease in dehydrosulphurenic acid treated U937 cells was shown. Therefore, the apoptosis induced by dehydrosulphurenic acid in tumor cells might not involve the mitochondrial pathway.

Example 8

The Effects of Dehydrosulphurenic Acid on Apoptosis-Related Proteins of Tumor Cells Involved in Death Receptor Pathway Death receptor pathway is a signal transduction pathway of apoptosis induction. Some of the death factors, such as TNF-α and so on, bind with death receptor (DR) such as TNF family in the membrane to send death signal to cells and induce a series of apoptotic events. A family of aspartic acid-specific proteases, known as caspases, includes caspase-3 and caspase-8 would be activated during apoptotic process. Activated caspase can cleave downstream protein such as Poly (ADP-ribose) polymerase (PARP) to proceed through apoptosis. This experiment investigated the implication of the death receptor pathway in dehydrosulphurenic acid-induced apoptosis through Western blot analysis.

Dehydrosulphurenic acid in the concentration of 5 μg/ml were used to treat human leukemic cell line U937 for 0.5, 1, 2, 4, and 16 hours; while U937 cells treated with 4 μM anti-cancer drug Camptothecin for 16 hours were served as positive control, and cells without treatment were served as negative control. All the proteins from the cells were extracted with bicinchoninic acid (BCA) assay kit (Pierce, Rockford, Ill.). Equal amounts (50 mg) of the protein were aliquoted and separated by electrophoresis on a 10% SDS-PAGE gel at a constant current of 20 mA and 70-100 volts. The proteins on the gel were transferred onto PVDF membranes, blocked with 5% non-fat milk, and incubated respectively with human-specific antibodies including: anti-Bcl-2, anti-Bax, anti-caspase 3, anti-caspase 8, anti-Cyclin B1, anti-p-Chk2 and anti-Actin (all were purchased from Transduction Laboratories, Lexington, Ky., USA) for 3 hours at room temperature. Secondary antibody horseradish peroxidase (purchased from Transduction Laboratories, Lexington, Ky., USA) was then added and the signals were detected under an Enhanced chemiluminescence system (ECS, Amersham Pharmacia, Piscataway, N.J.). The results were shown in FIG. 9.

Referring to FIG. 9, the expression of apoptosis- and mitotic catastrophe-related proteins after the treatments were shown. The Bcl-2 expression in U937 cells was slightly increased while Bax expression was not changed after dehydrosulphurenic acid treatment. In addition, expression of caspase-3 and caspase-8 was not altered by dehydrosulphurenic acid, and no cleavage of PARP was noted. However, cyclin B1 expression was up-regulated by dehydrosulphurenic acid, and phosphorylation of Chk2 was augmented.

These results indicated that the growth inhibition of dehydrosulphurenic acid to U937 cells might due to the cell death during mitosis.

In summary, dehydrosulphurenic acid isolated from *Antrodia cinnamomea* extracts can effectively inhibit the growth of human leukemic cells from U937 and human pancreatic cancer cells from BxPc-3. Results from cell cycle and observation of the morphology change revealed that dehydrosulphurenic acid inhibit the growth of pancreatic cancer cells from BxPc-3 through induction of apoptosis; and dehydrosulphurenic acid inhibit the growth of human leukemic cells from U937 through the mechanism of apoptosis and mitotic catastrophe, wherein dehydrosulphurenic acid had no effect on mitochondrial pathway as well as caspase in death receptor pathway. The mitotic catastrophe pathway was closely related to the checkpoint kinase activation. In addition, the up-regulation of cyclin B1 and increase in phosphorylation of Chk2 as described above indicated that the activation of Chk2 is involved with the induction of tumor cell death during mitotic stage by dehydrosulphurenic acid.

On the other hand, dehydrosulphurenic acid in the invention can be incorporated into medicinal compositions for treating the pancreatic cancer and leukemia to inhibit the growth of tumor cells. The medicinal compositions include not only the dehydrosulphurenic acid in effective doses, but also the pharmaceutically accepted carries. The carriers include, but are not limited to, excipients such as water, fillers such as sucrose or starch, binders such as cellulose derivatives, diluents, disintegrants, absorption enhancers or sweeteners. The composition according to the invention can be manufactured through mixing dehydrosulphurenic acid in effective doses with at least one of the carriers by means of conventional methods known in the pharmaceutically technical field, which can be formulated, but are not limited to, as a powder, tablet, capsule, pellets, granules or other liquid formulation.

What is claimed is:

1. A method for inhibiting growth of a tumor cell which comprises administering to a subject in need thereof an effective amount of a compound having the following formula:

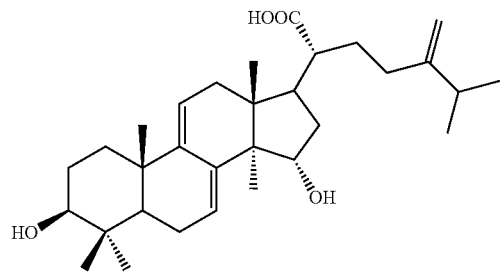

wherein the tumor cell is pancreatic cancer cell.

2. The method as claimed in claim 1, wherein the pancreatic cancer cell is from BxPc-3 cell line.

3. The method as claimed in claim 2, wherein the compound inhibit pancreatic cancer cell growth through apoptosis.

4. The method as claimed in claim 3, wherein the compound induces apoptosis of pancreatic cancer cell by inducing cell cycle arrest at G0/G1 phase and accumulating at sub-G1 population.

* * * * *